United States Patent
Knüttel

(10) Patent No.: US 6,970,252 B2
(45) Date of Patent: Nov. 29, 2005

(54) LOW-COHERENCE INTERFEROMETRIC DEVICE FOR DEPTH SCANNING AN OBJECT

(76) Inventor: Alexander Knüttel, Apfelstrasse 28, D-69488 Birkenau (DE)

( * ) Notice: Subject to any disclaimer, the term of this patent is extended or adjusted under 35 U.S.C. 154(b) by 289 days.

(21) Appl. No.: 10/311,241

(22) PCT Filed: Jun. 19, 2001

(86) PCT No.: PCT/DE01/02306
§ 371 (c)(1),
(2), (4) Date: Dec. 11, 2002

(87) PCT Pub. No.: WO02/04884
PCT Pub. Date: Jan. 17, 2002

(65) Prior Publication Data
US 2004/0090633 A1 May 13, 2004

(30) Foreign Application Priority Data
Jul. 7, 2000 (DE) .................................. 100 33 189

(51) Int. Cl.$^7$ ................................................ G01B 9/02
(52) U.S. Cl. ...................................................... 356/497
(58) Field of Search ............................... 356/497, 479, 356/519, 505, 511

(56) References Cited

U.S. PATENT DOCUMENTS

| 4,869,593 | A | | 9/1989 | Biegen |
| 5,579,112 | A | | 11/1996 | Sugiyama et al. |
| 5,847,827 | A | | 12/1998 | Fercher |
| 5,953,124 | A | * | 9/1999 | Deck ........................... 356/497 |
| 6,307,633 | B1 | * | 10/2001 | Mandella et al. ............ 356/479 |
| 6,556,305 | B1 | * | 4/2003 | Aziz et al. ................... 356/512 |
| 6,741,355 | B2 | * | 5/2004 | Drabarek ..................... 356/482 |

FOREIGN PATENT DOCUMENTS

| DE | 195 04 189 A1 | 8/1996 |
| DE | 195 14 860 A1 | 10/1996 |
| DE | 195 20 305 A1 | 12/1996 |
| DE | 196 24 167 A1 | 1/1997 |
| DE | 197 04 602 A1 | 8/1998 |

OTHER PUBLICATIONS

Alexander Knuttel, "Niederkoharenz-Interferometrishes Gerat", PCT WO 9727468 International Patent Cooperation Treaty.

(Continued)

Primary Examiner—Andrew H. Lee
(74) Attorney, Agent, or Firm—Walter A. Hackler

(57) ABSTRACT

Low-coherence interferometric device for light optical depth scanning of an object (13) positioned in front of a measurement aperture (12) of the device by detecting the position of light-reflecting sites which are located at different measurement depths within the object (13) along a scanning path (19) running into the object in a scanning direction (25) using a low-coherence interferometer which comprises a low-coherence light source (7), a beam splitter (8), a reference reflector (9) and a detector (10).

The interferometer is a free-space in-line interferometer (6) having a beam splitter (8) running transversal to the direction of scanning (25). The light transmitter (7), the detector (10) and the reference mirror (9) are arranged on the side of the beam splitter facing away from the measurement aperture.

A movable scanning lens (11) is arranged between the beam splitter (8) and the measurement aperture (12). The movable scanning lens (11) and the beam splitter (8) are movable for depth scanning in the same direction and in synchronization.

13 Claims, 6 Drawing Sheets

OTHER PUBLICATIONS

Eric Swanwson, "Method And Apparatus For Acquiring Images", PCT WO 95/33971 Internatioanl Patent Cooperation Treaty.

J.M. Schmitt, "Compact In-Line Interferometer For Low-Coherence Relectometry", Optics Letters, Feb. 15, 1995, vol. 20, No. 4, pp. 419-421, Optical Society of America.

* cited by examiner

LOW-COHERENCE INTERFEROMETRIC DEVICE FOR DEPTH SCANNING AN OBJECT

The invention relates to a low-coherence interferometric device for light optical depth scanning of an object positioned in front of a measurement aperture of the device by detecting the position of light-reflecting sites located at different depths within the object along a scanning path extending into the object in a scanning direction.

Such low-coherence interferometric methods are used to investigate various objects. They are referred to below as LCDS (low-coherence depth scan) methods. In many applications, it is sufficient to investigate the object one-dimensionally, i.e., exclusively on a certain scanning path extending into the depth of the object in order to obtain information regarding reflecting structures. In such cases, a strict depth scan or longitudinal scan is sufficient. However, in most applications, information regarding reflecting structures in a plane extending into the object or even information regarding a partial volume is to be obtained by an additional lateral scan. This requires a two-dimensional or three-dimensional scan which is implemented in the simplest case by lateral displacement of the interferometer in one or two dimensions on the surface in small increments. Such methods permit multidimensional imaging and are usually referred to as OCT (optical coherence tomography) methods. The invention is in particular suitable for OCT methods.

In the medical field, LCDS methods (including OCT) are used mainly in conjunction with examination of areas of body parts that are near the surface and readily accessible (eyes, skin, nails). One very interesting area of use is endoscopy, e.g., of the bronchial tubes or the gastrointestinal tract, but this requires an extreme miniaturization of the device. In the non-medical area, there is interest in measuring various semi-transparent light scattering objects (e.g., layers of plastic or ceramic).

A common feature of all LCDS methods is that light of a low-coherence light source (emitting spectrally in a broad band) is divided into two partial beams, namely a measurement light beam which penetrates into the sample and a reference light beam which is split, the two partial beams being combined, before striking a detector, such that an interference signal is generated. To this end, the device contains an interferometer arrangement which includes the beam splitter, a reference reflector and the detector, in addition to the low-coherence light source. The light paths between these elements form so-called interferometer arms. The light of the light source passes through the light source arm to the beam splitter where it is split. A first part of the light is irradiated as measurement light via an object arm into the sample, while a second part runs as reference light via a reflector arm to the reference reflector. Both light components are reflected (the measurement light at light-reflecting sites in the object, and the reference light on the reference reflector) and are returned to the beam splitter on the same light path (object arm or reference arm). There they are combined and sent via a detector arm to the detector where an interference signal is measurable on the light-sensitive surface due to the interference of the two partial beams.

A prerequisite for the occurrence of interference is that the difference of the optical light path length in the reference arm (from the beam splitter to the reference reflector) from the optical path length traveled by the measurement light between the beam splitter and the respective reflecting site in the investigated object is not more than the coherence length of the light source. Only if this condition is met an interference signal is measured.

The LCDS method is used to investigate structures in the interior of light-scattering objects. By varying the ratio of the length of the reference arm to the length of the object arm, different LCDS measurement depths for which the interference condition explained above is met can be set along a scan path which extends into the investigated object in the scanning direction. The length of the reference light path thus defines which site in the object is examined by interferometry. The current interferometric measurement position is the position in the measurement beam path for which the optical length of the measurement light path from the beam splitting to the beam merging is the same as the optical length of the reference light path from the beam splitting to the beam merging. Since the length of the reference light path of a given device is known, the length of the measurement light path to the light reflecting site, referred to hereafter as the reflection site, can be determined.

Generally, the LCDS measurement depth is set by shifting the reference mirror in the direction of the reference beam and thereby decreasing or increasing the length of the reference light path. The position of the reference mirror determines the LCDS measurement depth in the interior of the object (i.e., the current examination position). The strength of the interference signal (which is processed by A/D conversion and subsequent rectification, for example) is a measure of the strength of the light reflection at the reflection site in the LCDS measurement depth.

Details concerning various known LCDS devices may be obtained from the relevant literature, including the following publications:
1) WO 95/33971
2) J. M. Schmitt "Compact in-line interferometer for low-coherence reflectometry"
3) U.S. Pat. No. 5,847,827
4) WO 97/27468
5) U.S. Pat. No. 5,579,112

The maximum resolution of LCDS devices in the scanning direction (Z direction) corresponds to the coherence length of the measurement light used. With suitable light sources (e.g., superluminescent diodes) this amounts to approx. 10 $\mu$m, so the resolution that can be achieved in Z direction also amounts to about 10 $\mu$m. A comparable resolution in lateral direction (X and Y direction) can be achieved only when the measurement light is focused. In citations 2) through 4), an optical focusing by means of a convergent lens is described. In citation 5), the required focusing is to be ensured with electronic means. The focusing of the measurement light is advantageous not only with regard to the lateral resolution, but also leads to an increase in the measured intensity, because the light is irradiated from a larger solid angle and the measurement can be based on the light detected in a larger solid angle. As consequence more light can be captured with increasing numerical aperture of the focusing lens.

Use of a focusing lens in the LCDS method and in particular in the OCT method is associated with a fundamental problem. Since the LCDS measurement depth changes constantly during depth scanning, it is necessary to design the focusing lens so that the depth of focus at all times corresponds to the LCDS measurement depth ("focus correction"). This can in principle be achieved by adjusting the focusing lens in synchronization with the LCDS measurement depth. However, this requires a great technical expenditure for the desired rapid scanning or may even be impossible.

Furthermore, the correspondence between the LCDS measurement depth and the depth of focus during movement in the Z direction becomes worse as the refractive index N becomes greater. This is attributed to the fact that with a displacement by $\Delta z$, the measurement depth in the object changes by less than $\Delta z$, namely by $\Delta z_i = \Delta z/N$, while the depth of focus is shifted by more than $\Delta z$, namely by approximately $\Delta z_f = \Delta z * N$. Consequently, the depth of focus and the LCDS measurement depth do not match over the entire scanning path (for $N \neq 1$) even if the interferometer unit as a whole is moved for depth scanning. This problem is referred to below as the "refractive index problem."

To the extent that citations 1) through 5) address these problems, they contain the following proposals for solving it.

According to citation 2), the entire unit consisting of the light source, mirror, lenses and beam splitter is moved in the scanning direction for depth scanning. Therefore, the depth of focus moves in the same direction as the LCDS measurement depth. However, only a very low scan rate is possible, because a large and heavy unit must be moved as a whole.

Citation 4) also describes a device in which depth scanning is accomplished by moving a unit comprising the light source, the beam splitter and the detector. In this case, a compact design, low weight and thus a higher scan rate are achieved by miniaturization of the interferometer unit using an optical chip plus additional special measures. To solve the refractive index problems this citation proposes focus correcting means, which can be positioned between the interferometer unit and the measurement object. This makes it possible to achieve a very good correspondence between the depth of focus and the LCDS measurement depth, but it would be desirable to reduce the design complexity and size associated of the device.

In the device described in citation 3), the depth of focus and the LCDS measurement depth are adjusted by means of an additional reflector which is arranged in the measurement arm and simultaneously has focusing properties. This requires an additional beam splitting by means of a second beam splitter arranged in the measurement arm. The measurement light beam passes the beam splitter four times. This complex design results in a large structural volume, and furthermore the measurement light is greatly attenuated by the multiple beam splitting and thus the signal-to-noise ratio is reduced.

Citation 5) describes an OCT device in which focusing is said to be achieved by electronic means only. In principle, however, electronic focusing is inferior to optical focusing. This is true in particular in the case of optical measurement arrangements having a large numerical aperture. A large numerical aperture is, however, necessary with OCT devices for reasons of signal intensity and image definition. In addition, electronic focusing is applicable only to secondary light reflected out of the sample, not to primary light directed into the sample.

On this basis, the present invention addresses the problem of making available a low-coherence interferometric device for depth scanning which permits a synchronous adjustment of the LCDS measurement depth and the depth of focus in a simple design with the fewest possible moving parts and compact dimensions.

This problem is solved by a low-coherence interferometric device having the general features explained above, where the interferometer is a free-space in-line interferometer having a beam splitter plate running transverse to the scanning direction, wherein the light transmitter, the detector and the reference mirror are arranged on the side of the beam splitter plate facing away from the measurement aperture, the light source arm and the reference arm are located at least in their sections adjacent to the beam splitter at the same angle to the surface of the beam splitter facing them, a movable scanning lens is located between the beam splitter plate and the measurement aperture, and the scanning lens and the beam splitter plate are movable in the same direction as and in synchronization with the depth scanning.

The following advantages are, inter alia, achieved by the invention:

A very compact design is possible. Surprisingly, the free-space design according to the invention is superior to designs known in the past which work with optical fibers or optical chips.

The focus correction is accomplished by movement of only two components in the same direction, the components preferably being rigidly connected together in the form of a commonly movable scanning module.

The invention offers the possibility of adjusting the numerical aperture on the light path of the light directed into the object (primary light) differently from the light reflected out of the measurement object (secondary light). Preferably the numerical aperture of the primary light path is smaller than the numerical aperture of the secondary light path.

The invention permits several additional improvements in signal quality which are explained in greater detail below.

An example of a known free-space in-line interferometer is described in citation 2). Another embodiment is disclosed in

6) DE 195 04 189 A1.

However, this prior art publication does not contain any reference to the fact that the problem of focus correction in LCDS devices can be solved in an extraordinarily advantageous manner by means of this design principle in combination with the additional features of the invention.

The invention is explained in greater detail below on the basis of exemplary embodiments illustrated in the figures. The particular details described may be used individually or in any combination to create preferred embodiments of the invention.

Figure 1:
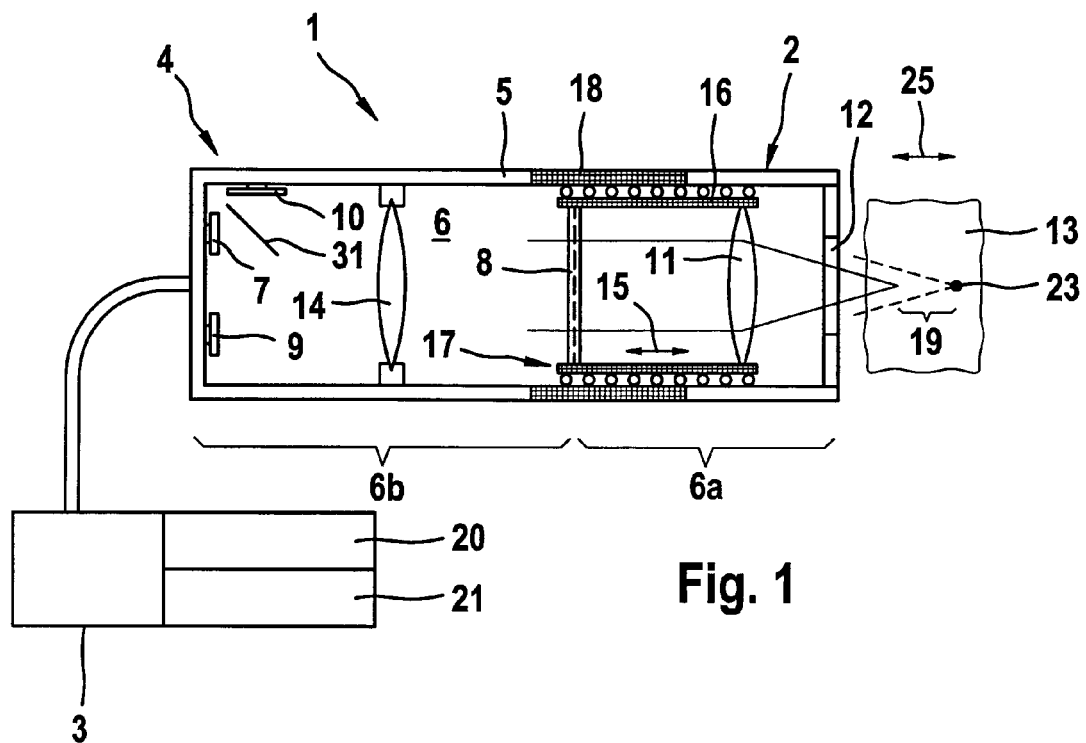
FIG. 1 shows a device according to the invention, partially as a schematic sectional view and partially as a block diagram.

The LCDS device 1 illustrated in FIG. 1 consists essentially of a measurement head 2 and an electronic unit 3, which is shown only schematically as a block, and is connected by a cable to the measurement head 2.

Housing 5 of measurement head 2 contains the optical elements of a low-coherence interferometer 6, namely a low-coherence light source 7, a beam splitter 8, a reference reflector 9 and a detector 10. The beam splitter 8 separates the in-line arrangement of interferometer 6 into a scan section 6a facing measurement object 13 and a detection section 6b. It is preferably designed in the form of a plate in the sense that its length and width dimensions are larger in comparison with its thickness. Without restriction of a general understanding the term beam splitter plate is used hereafter. In the simplest case, the beam splitter plate may consist of a homogeneous optical glass having a smooth surface, optionally coated to adjust the beam splitter ratio. However, as illustrated below on the basis of another embodiment, it may also have a more complicated structure having different transmission properties in different area segments and/or a profiled surface structure.

Two lenses are provided in housing 5. A first lens, referred to hereafter as the scanning lens 11, is positioned in the scanning section 6a between the beam splitter plate 8 and a measurement aperture 12 through which the measured light is irradiated into an test object 13 placed in front of the measurement aperture. A second lens, referred to below as the detecting lens 14, is positioned in the detection section 6b between the beam splitter plate 8 and a light transmitter/receiver device 4 formed by the light transmitter 7, detector 10 and reference reflector 9. Lenses 11 and 14 are each designed as simple lenses, but in practice they may also comprise a plurality of lenses.

Beam splitter plate 8 and scanning lens 11 are movable for depth scanning in the same direction and in synchronization. In the preferred embodiment illustrated here, they are rigidly connected together—as components of a scanning module 16. For movement of the scanning module 16 (thus for joint movement of the beam splitter plate 8 and scanning lens 11) in the scanning direction represented by arrow 15 which direction extends transverse to the plane of the beam splitter plate, there is a linear drive 17 which may be implemented, for example, electromagnetically by means of a coil 18 surrounding the scanning module 16, as illustrated here. The movement of scanning module 16 causes a corresponding shift of the reflection site 23 observed with the LCDS device along a scanning path 19.

Electronic unit 3 contains the electronic elements required for operation of measurement head 2 and for analysis of the signals thus obtained. This includes a control unit 20 for controlling the scanning movement and an electronic analyzer 21 for analysis of the interference signals. The analyzer unit 21 and the method used for analysis of the interference signal do not have any special features. In this regard, reference can be made to the pertinent literature.

Figure 2:
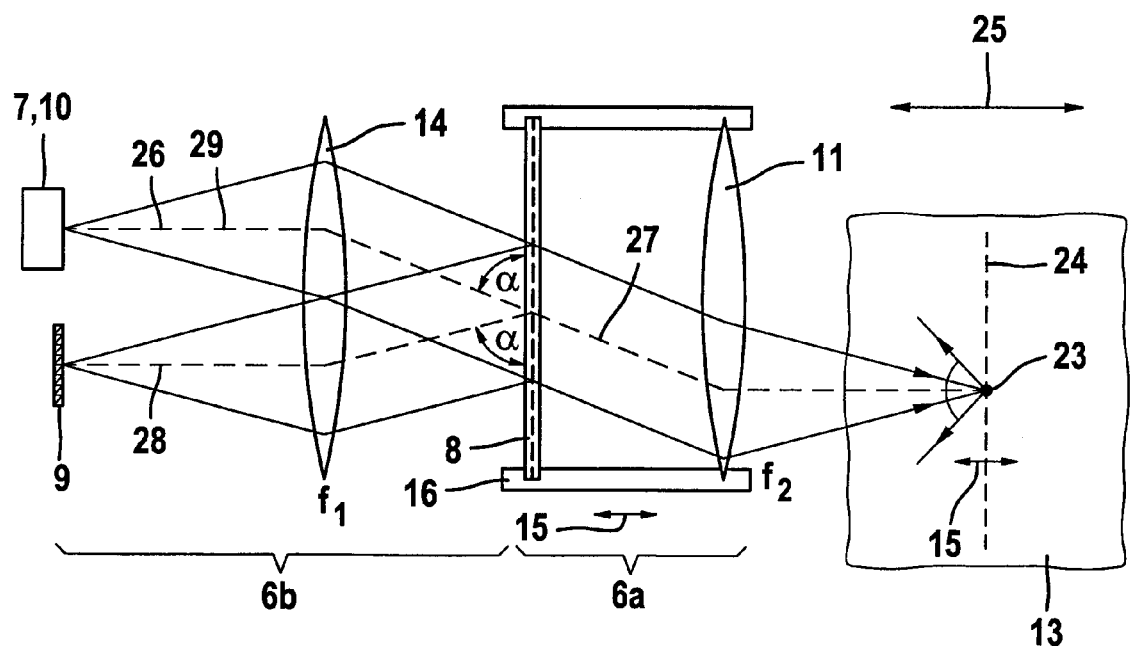
FIG. 2 shows principles of the beam path in a device according to the invention.

FIG. 2 shows a combined light transmitter-detector element 7, 10 in which the light transmitter and detector are located in close spatial proximity, as explained in greater detail below. The primary light emitted by light transmitter 7 is collimated by detecting lens 14 and strikes beam splitter plate 8 as parallel beam. Beam splitter plate 8 splits the light into a component that passes through and into a reflected component. The reflected light is focused on the reference mirror 9 by the detecting lens, is reflected there and, after being reflected again on the beam splitter plate, impinges back onto detector 10.

The light passing through beam splitter plate 8 is focused by scanning lens 11 in a focusing plane 24 in the test object 13. When the light is reflected at a reflection site 23 by a reflective structural element present in the test object 13, it passes through the scanning lens 11 and beam splitter plate 8 as well as detecting lens 14 and returns to detector 10.

The light paths between elements 7, 8, 9 and 10 form interferometer arms of a free-space in-line interferometer, namely a light source arm 26 between light source 7 and beam splitter 8, an object arm 27 between beam splitter 8 and reflection site 23 in object 13, a reference arm 28 between beam splitter 8 and reference reflector 9 and a detector arm 29 between beam splitter 8 and detector 10.

Beam splitter plate 8 is oriented transversal to the scanning direction represented by arrows 15 and corresponding to the optical axis of lenses 11 and 14. The scanning module formed essentially from beam splitter plate 8 and scanning lens 11 is movable for depth scanning in the scanning direction 15. The reflection on scanning plate 8 results in the reference arm forming the same angle α to the beam splitter plate 8 as does light source arm 26, at least in the section of the reference arm adjacent to the beam splitter plate. The light source arm 26 and detecting arm 29 run coaxially at least in the section adjacent to beam splitter plate 8.

Figure 3:
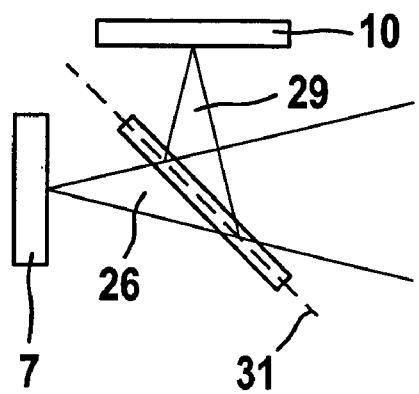
FIG. 3 shows a portion of the beam path in an alternative embodiment.

In the arrangement illustrated in FIG. 3, a semi-transparent mirror 31 is provided in the path of the light of light source arm 26 and coaxial detector arm 29, so that primary light coming from light source 7 passes through this mirror and reflection of the detecting light in the direction of detector 10 takes place at the surface of this mirror which faces beam splitter plate 8. Therefore the light transmitter 7 and detector 10 are spatially separated. The light source arm 26 runs in the section adjacent to light transmitter 7 separately from the section of detector arm 29 adjacent to detector 10.

The arrangement illustrated here—like other interferometer arrangements—achieves the result that the light reflected on reference mirror 9 on the one hand and on the reflection site 23 in the object 13 on the other hand strikes the same light-receiving surface of detector 10. This leads to interference when the optical path of the measurement light (consisting of the light source arm 26, object arm 27 and detection arm 29) differs from the optical light path of the reference light (consisting of the light source arm 26, reference arm 28 and detection arm 29) by less than the coherence length of the light. Since this is, with a suitable choice of light source, on the order of 10 μm the depth scanning permits a resolution of this order of magnitude.

Movement of the scanning module 16 in direction 15 by an amount $\Delta z$ in the direction of the test object 13 (from left to right in FIG. 2) leads to an increase of the optical path of the reference light to approximately $2\Delta z$. Accordingly, the LCDS measurement depth is shifted into the test object by $2\Delta z/N$, where N is the refractive index of the test object. The same movement of scanning module 16 by $\Delta z$ leads to a displacement of the focus plane 24 by $\Delta z*N$ due to the movement of scanning lens 11 coupled with the beam splitter. By equating these conditions one may derive that the two displacements are equal for a refractive index of $N=\sqrt{2}=1.414$.

Figure 4:
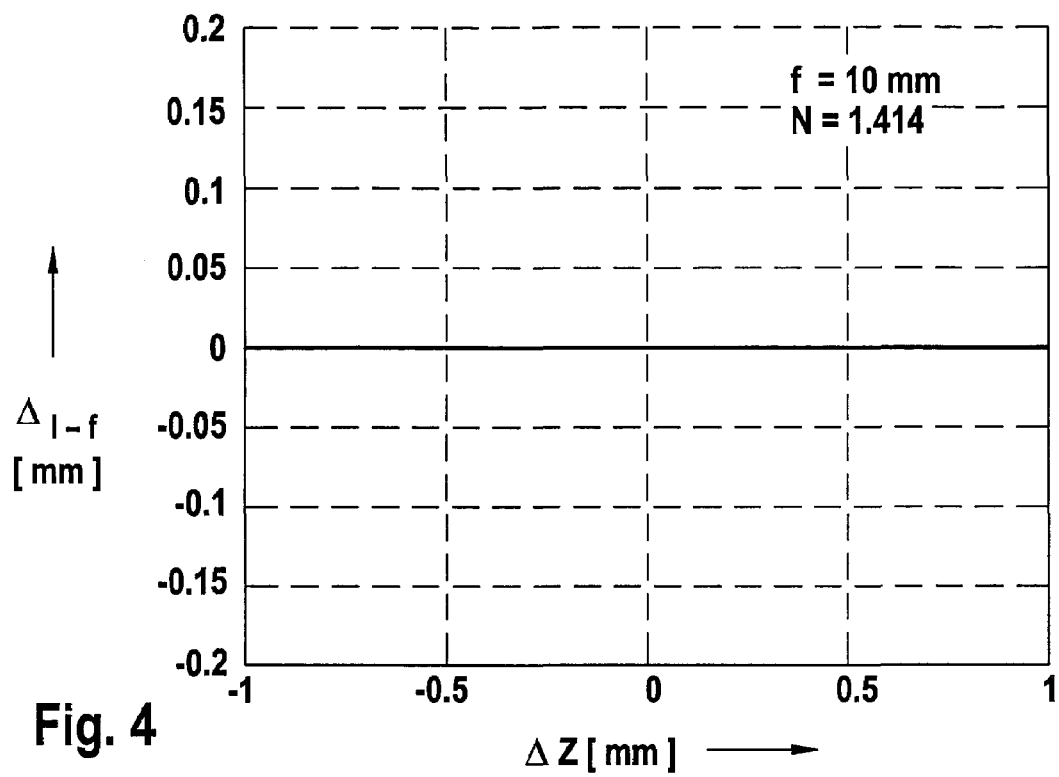
FIG. 4 shows a diagram of the deviation in the focus correction in the case of an ideal refractive index of the sample.
Figure 5:
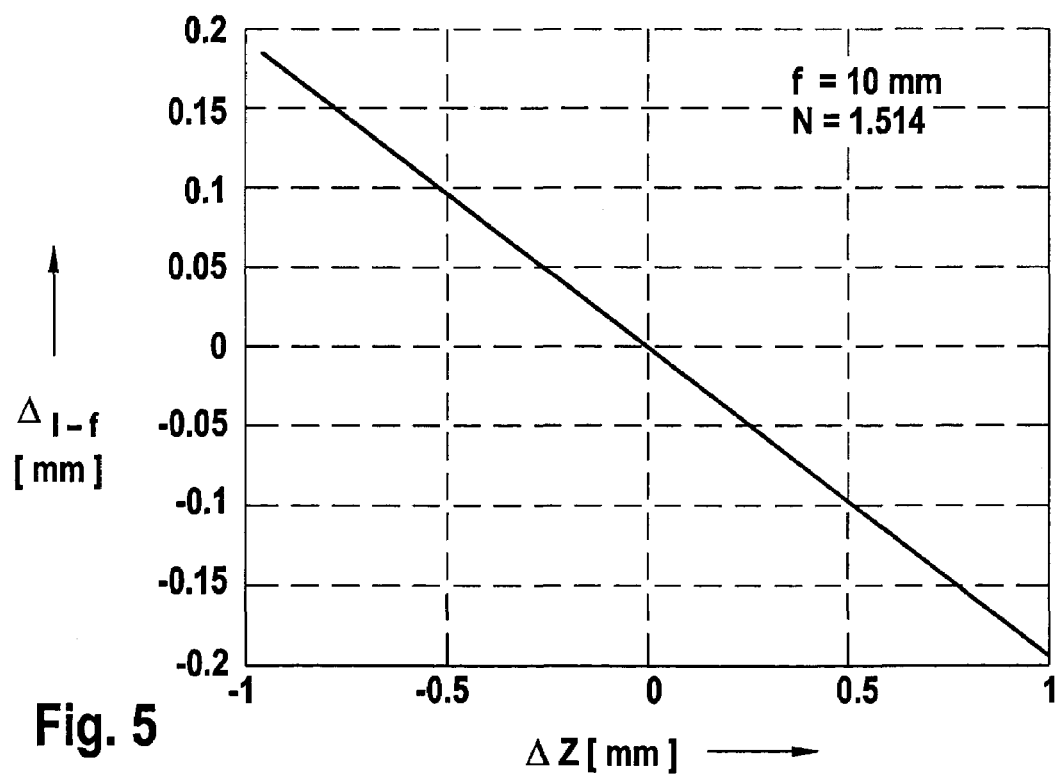
FIG. 5 shows a diagram of the deviation in the focus correction in the case of a refractive index of the sample differing from the ideal value.

FIG. 4 illustrates this relationship graphically for a scanning lens having a focal length $f_2=10$ mm, where the difference $\Delta_{1-f}$ (difference between the LCDS measurement depth and the depth of focus in mm) is plotted as a function of the displacement $\Delta z$ of the scanning module 16 (also in mm). It can be seen here that the focus deviation is zero for a refractive index N=1.414. However, FIG. 5 shows a similar diagram for a refractive index of N=1.514 with a considerable deviation in the focus correction.

Since the average refractive index in human skin is relatively close to a value of 1.414, the particularly simple embodiment of this invention illustrated in FIGS. 1 and 2 can be used with good results for medical studies on biological tissue, in particular skin tissue. However, if test objects (medical or non-medical) whose refractive index differs significantly from this value are to be examined with a low focus deviation over a larger $\Delta z$ range, then additional measures according to preferred embodiments of this invention are recommended.

In particular, it may be expedient to design the linear drive 17, which is used to move the beam splitter plate 8 and the scanning lens 11, so that the beam splitter plate 8 and the scanning lens 11 are moved in the same direction (scanning direction 15) and in synchronization but not at the same speed. The two speeds are preferably in a fixed ratio to each other; for example the speed of movement of scanning lens 11 may amount to 90% or 110% of the speed of movement of the beam splitter plate 8 in each phase of movement. Consequently the displacement of the depth of focus is larger or smaller than a given displacement of the beam splitter plate 8, so that the exact focus correction (focus deviation 0) is achieved at a different value of the refractive index. The speed ratio of the movements of beam splitter plate 8 and scanning lens 11 required in the individual case can be determined empirically or—on the basis of the considerations explained above—by calculation. The means required for implementation of such a displacement in a defined speed ratio are common knowledge to those skilled in the art. For example, corresponding electronically controlled actuator drives may be used. A mechanical linkage, e.g., by drive levers, may also be used for implementation of the desired ratio of the driving speeds.

Figure 6:
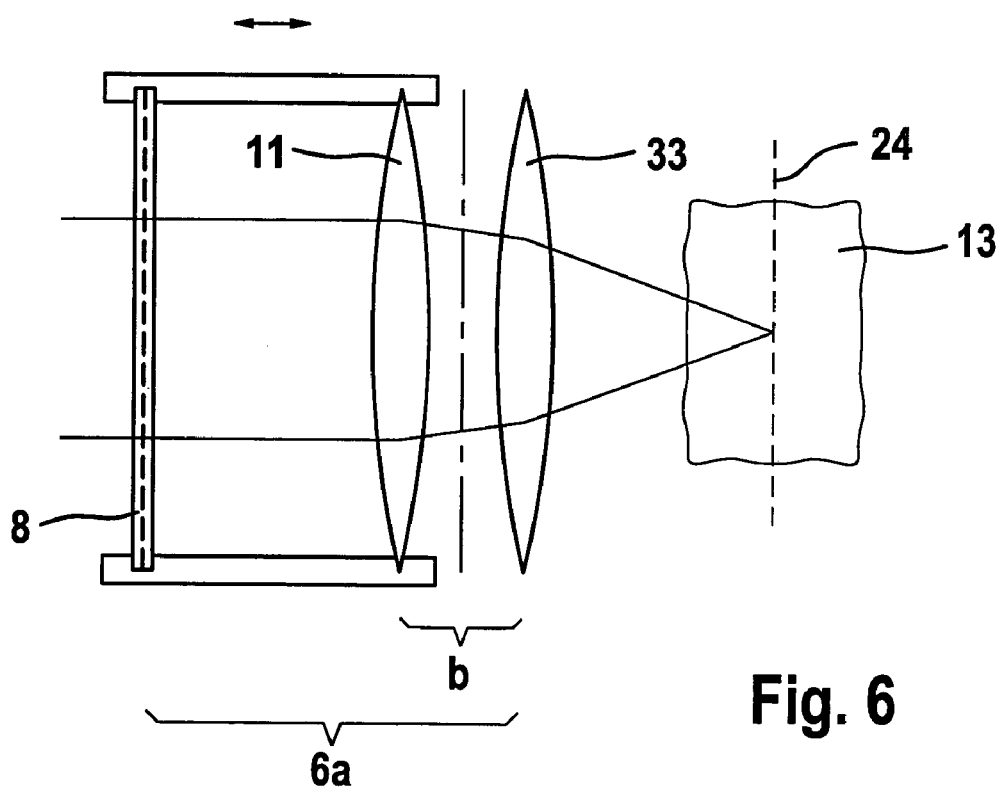
FIG. 6 shows a schematic view of the principles of a portion of the beam path corresponding to FIG. 2 in the case of an alternative embodiment which allows an adaptation to different refractive indices of the sample.

FIG. 6 shows an embodiment of the invention according to which an almost perfect correction of focus can be achieved for any desired refractive index with a minimum of structural complexity. In the scanning section 6a between the movable scanning lens 11 and the test object 13, an additional stationary lens 33 is located as close as possible to scanning lens 11, whereby the focusing of the measurement light in the focus plane 24 is achieved by the joint effect of the two lenses 11, 33. On the basis of geometric optical rules, it can be shown that with such an arrangement the displacement of the movable scanning lens 11 by the amount $\Delta z$ leads to a displacement in the focus plane by $\Delta z * N * a^2$, where a is a splitter factor which describes the ratio of the individual focal lengths $f_1$ and $f_2$ as contributions to the total focal length f of the combination consisting of lenses 11 and 33 ($f_1=f/a$; $f_2=f/(1-a)$).

If this result is in turn equated to the displacement of the LCDS measurement depth, this yields a perfect correction of focus for $N=\sqrt{2}/a$. The splitter factor a of lens combination 11, 33 must be selected so that the refractive index of the respective test object results. With values of a <1, it is possible to implement refractive indices greater than 1.414.

If the refractive index of the test object is less than 1.414, a must be greater than 1. This corresponds to a case in which the stationary lens 33 has a negative focal length, i.e., dispersing properties.

Figure 7:
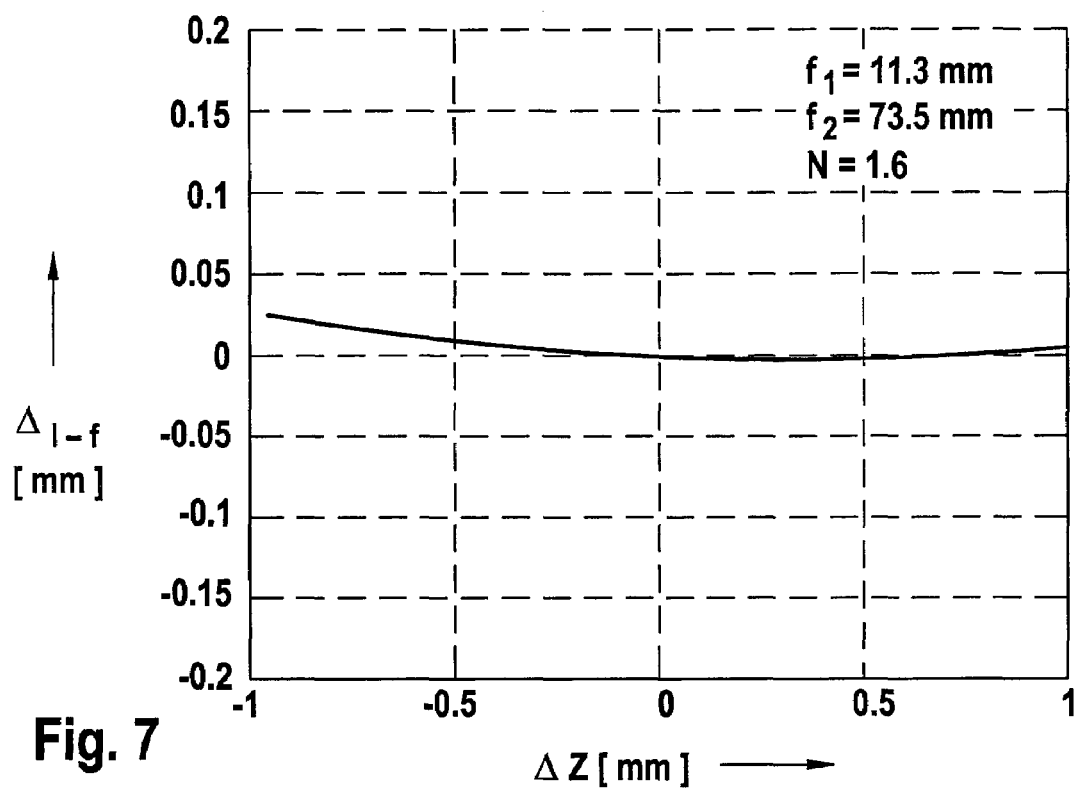
FIG. 7 shows a diagram of the deviation of the focus correction by means of the embodiment illustrated in FIG. 6 with a good adaptation to the refractive index of the sample.

FIG. 7 shows a diagram according to FIG. 4 for a case which is optimized to a refractive index of the test object of N=1.6, where the focal lengths of the lenses are $f_1=11.3$ mm and $f_2=73.5$ mm. A slight deviation from the perfect focus correction can be seen which is caused by the fact that the considerations described above are based on the assumption that the distance b of the lenses 11, 13 is much smaller than the sum of their focal lengths. To approximate this condition as closely as possible, it is advantageous if the stationary lens 33 is placed as close as possible to movable scanning lens 11 and if both lenses have a small thickness. Therefore they are preferably each designed as simple lenses.

Figure 8:
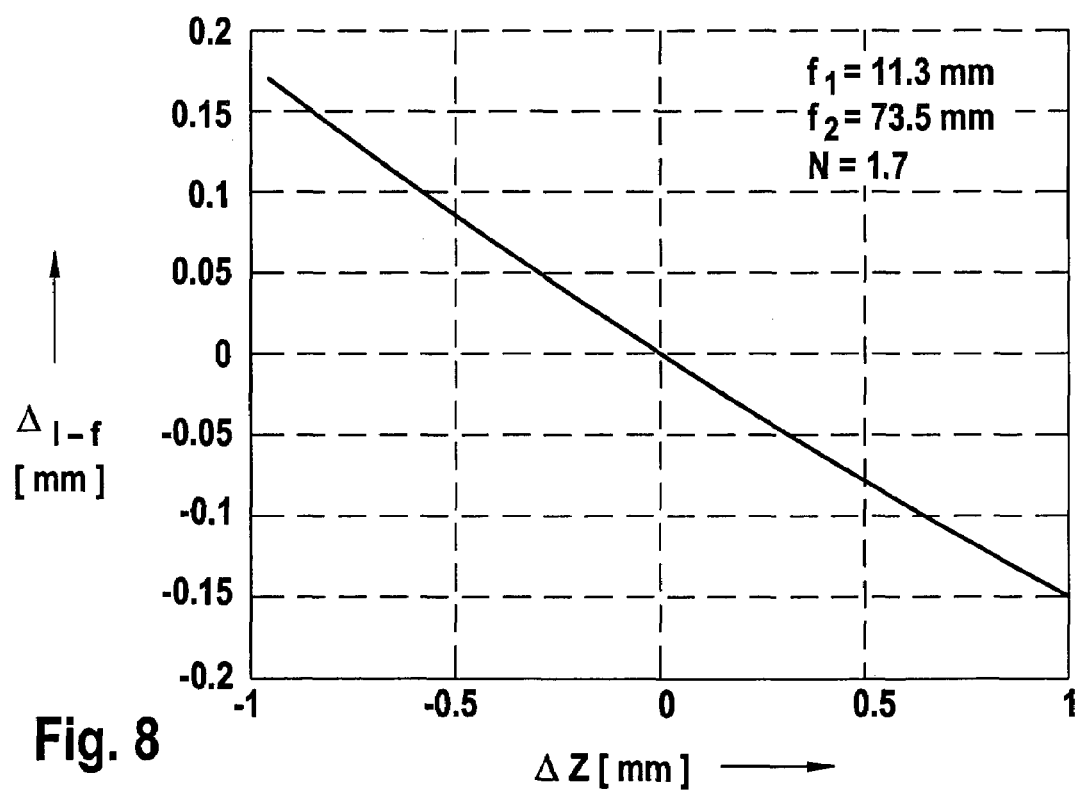
FIG. 8 shows a diagram of the deviation in the focus correction by means of the embodiment illustrated in FIG. 6 with an inferior adaptation to the refractive index of the sample.

FIG. 8 shows that in this case again the deviation from the refractive index setpoint leads to a great error of the focus correction.

As mentioned above, the invention is suitable in particular for OCT methods. The required two- or three-dimensional scanning is preferably achieved by a design in which the light transmitter 7 extends one-dimensionally along a line or two-dimensionally in a plane and the detector is formed by a corresponding linear or two-dimensional array of discrete light-sensitive areas. Thereby an OCT image with excellent lateral resolution is achieved in an image field whose dimensions correspond to the dimensions of the light transmitter and/or the detector array, without requiring additional actuators for a lateral displacement of the detection site.

Figure 9:
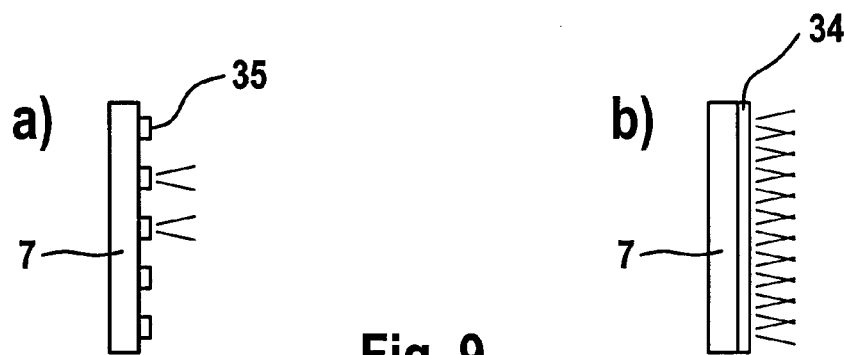
FIG. 9 shows schematic side views of four different embodiments of a light transmitter suitable for the invention.
Figure 9:
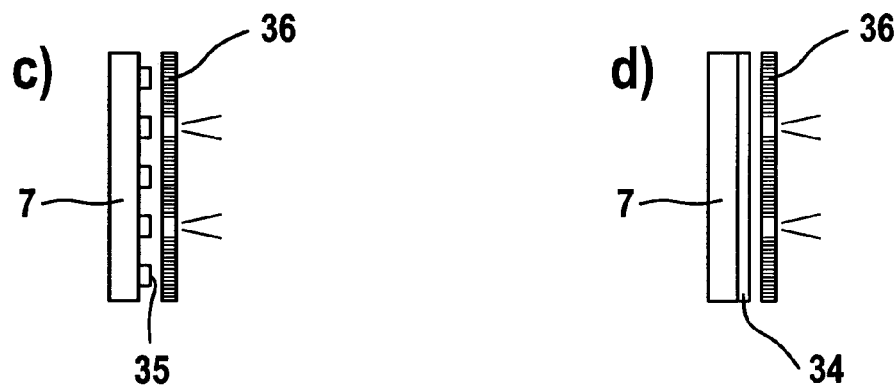

FIG. 9 shows schematically four different designs of a suitable light transmitter unit 7. According to FIG. 9a, a light source array with discrete emitters 35 may be used, wherein the emitters may be arranged one-dimensionally along a line or two-dimensionally (e.g., in the form of a checkerboard) in a plane. The individual emitters may be formed by discrete light-emitting semiconductor elements (edge or surface emitters of an LED) or an array of optical fibers. FIG. 9b shows that as an alternative, an area transmitter may also be used.

To reduce crosstalk between adjacent light-emitting points, it may be appropriate to arrange an electronic light-scattering element, in particular an SLM (spatial light modulator) in front of the light transmitter unit 7. FIG. 9c shows an SLM 36 which is operated so that at any point in time only the light of every second emitter 35 is allowed to pass through. This increases the distance between the active emitters and reduces crosstalk. The same is true for the arrangement illustrated in FIG. 9d where an SLM 36 is positioned in front of an area emitter 34.

Figure 10:
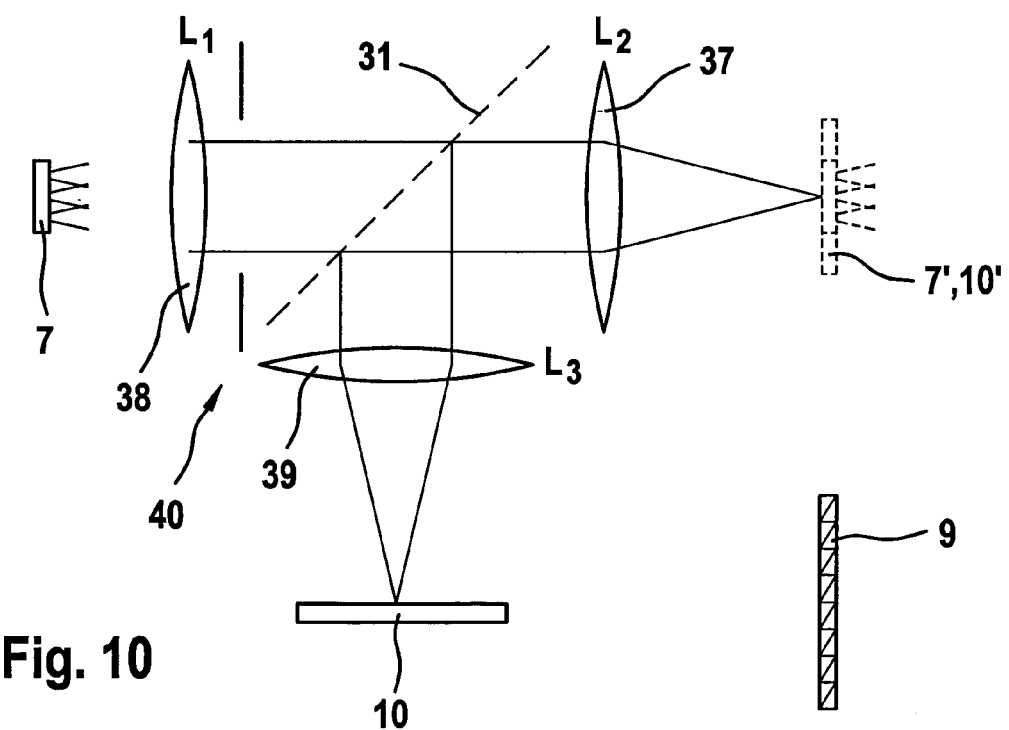
FIG. 10 shows a portion of the beam path of a further alternative embodiment of a device according to the invention.

As already explained on the basis of FIG. 3, it may be expedient to spatially separate the light source 7 and the detector 10 by means of a semitransparent mirror 31 (and at the same time maintain the coaxial optical arrangement required as part of the invention). In this regard, FIG. 10 shows a preferred embodiment in which a real image 7', 10' (represented by dotted lines) of the separately positioned components the light transmitter 7 and detector array 10 is created at the location of the light transmitter-detector unit 7, 10 in FIG. 2 by means of an optical system 40 consisting of three lenses 37, 38 and 39 and a semitransparent mirror 31. In relation to FIG. 3, the advantage of this arrangement is that the light passes through the semitransparent mirror 31 as a largely parallel beam of light and this prevents errors due to angle-dependent beam splitter ratios of the semitransparent mirror 31. In addition, such an arrangement permits an individual adaptation of the lens to the requirements of the light transmitter 7 on the one hand and detector 10 on the other hand. In particular, the real image 10' of the detector is smaller than the physical detector array 10. In other words, the optical system 40 has magnifying properties with respect to the detector 10. Therefore, it is possible to achieve a very high resolution (better than 10 μm) using commercially available light-sensitive elements (the diameter of which is usually greater than 10 μm). Such an arrangement is also advantageous with regard to the signal-to-noise ratio.

Figure 11:
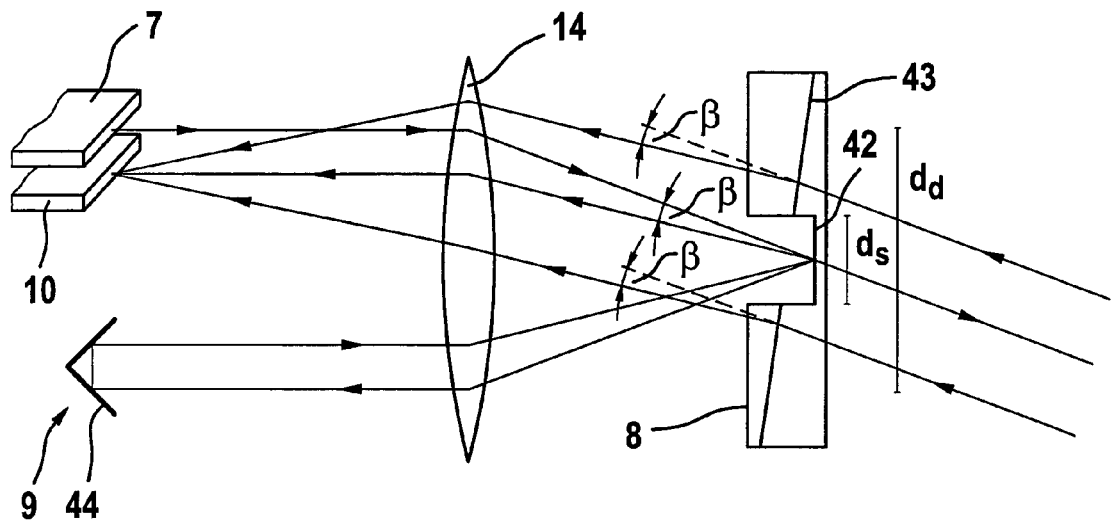
FIG. 11 shows a portion of the beam path of a further alternative embodiment of a device according to the invention and FIG. 12 shows a schematic diagram of a device for additional electronic focus correction.

FIG. 11 shows an arrangement by means of which a semitransparent mirror 31 separating the light path to detector 10 from the light-path over which the primary light is emitted by light transmitter 7 is avoided. It is assumed here that the primary light is emitted by the light transmitter 7 at a much smaller angle (i.e., with a smaller numerical aperture) than the angle at which detector 10 receives the light (with a high numerical aperture). This can be implemented easily with the free-space arrangement according to the invention and is also advantageous in other regards.

With the arrangement illustrated in FIG. 11, a light source 7 and a detector 10 are arranged in close spatial proximity. Combined light transmitter-detector modules may also be used, where one-dimensional light source arrays are arranged side-by-side with one-dimensional detector arrays or two-dimensional light source arrays are arranged next to two-dimensional detector arrays.

The light of light source 7 is collimated by detection lens 14 and, because of the smaller numerical aperture, it passes through a window area 42 having a relatively small diameter $d_s$ in a beam splitter plate 8. The beam splitter plate 8 has different transmission properties in different areas. In window area 42, it allows the primary light to pass without deflection and reflects a predetermined portion, e.g., 50% in the direction of the reference reflector 9. In the remaining area 43 (outside of window area 42) it has the property of causing a parallel beam passing through to be tilted slightly by an angle β. After reflection from test object 13, the light strikes the beam splitter plate 8 with a larger numerical aperture within a larger diameter $d_d$. In this way the further beam path is tilted in the direction of detector 10. Of course, a corresponding slight change in the direction of the beam by angle β must also take place with regard to the reference light. This may be accomplished easily, as illustrated in FIG. 11, by using a reflecting prism 44 as reference mirror 9.

Tilting of the beam direction by angle β can be accomplished through a corresponding structure of the beam splitter plate 8 in a manner with which those skilled in the art are familiar. For example, as shown here, the plate may be composed of sections of optical glass having different refractive indexes arranged in a wedge shape. The beam splitter plate 8 differs in subareas 42 and 43 not only with regard to its directional transmission properties (tilting of the beam direction) but also with regard to its transmission properties pertaining to the intensity. In the case illustrated here, in subareas 43 it is provided on the side facing the measurement object with a coating that prevents reflection as much as possible, so that only the smallest possible portion of the secondary light which is reflected by the measurement object and strikes beam splitter plate 8 is reflected at the surface, and thus the light reaches detector 10 as completely as possible.

Apart from a slight tilting by an angle β of 20° at most, preferably at most 15°, the optical axes of the secondary light striking detector 10 from the beam splitter plate and of the primary light emitted by the light transmitter 7 in the direction of the beam splitter plate 8 should essentially correspond, i.e., the light source arm 26 and detection arm 28 should run approximately coaxially.

The separation of the detection arm of the interferometer from the light source arm without using a semitransparent mirror, as illustrated on the basis of the example shown in FIG. 11, has the advantage that it avoids the attenuation of the light intensity usually caused by such mirror.

Figure 12:
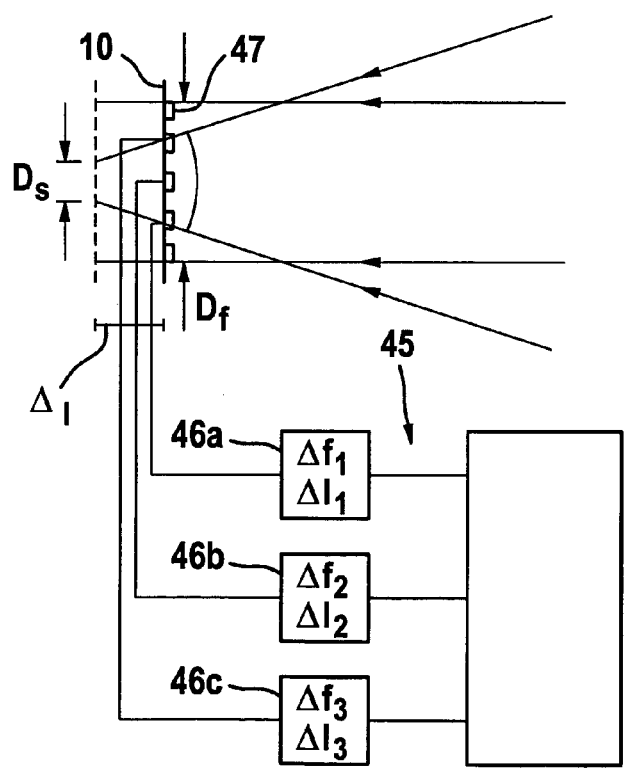

FIG. 12 shows another preferred embodiment in which an electronic focus correction is additionally used. A focus-correcting circuit 45 is provided here (as part of electronic unit 3), including delay elements 46a to 46c which make it possible to selectively delay the signals generated by different discrete light-sensitive elements 47 of a detector array.

Such a focus correction may be used to advantage in many regards within the scope of this invention. First, it may serve to compensate for known static focusing errors such as those caused by aberrations in lenses 11 and 14 (or other optical imaging elements of the system). This makes it possible to work with small, simple and inexpensive lenses.

In addition, focusing errors caused by statistical fluctuations in refractive index which are not known may also be corrected. They may result, for example, from the fact that the surface of the test object is not exactly planar. As part of the LCDS measurement, the surface of lens 13 is detected as a strong reflection signal. This information can be processed in electronic unit 3 to form a dynamic image of the surface structure and used to compensate for the different optical path lengths and the resulting light transit times in the test object 13.

The invention allows on the whole an extraordinarily space-saving design in particular with regard to the diameter of the arrangement which is shown only in highly schematized form in FIG. 1. In particular endoscopic examinations are possible. When using a light transmitter and detector array extending in one or two dimensions, a very good high resolution image can be obtained in both lateral and longitudinal directions, and only one motion drive in the longitudinal direction is required. By means of an appropriate choice of the splitter ratio of the beam splitter plate 8, it is possible to adjust the intensity ratio of the detected light in relation to the incident primary light in order to optimize the signal-to-noise ratio. Preferably a design which is symmetrical, also in Z direction, at least with regard to dispersion, is selected, i.e., lenses 11 and 14 (and/or in the embodiment according to FIG. 6, lens combination 11/33 and lens 14) have approximately the same dispersion properties. Thereby problems with different dispersion in the interferometer arms are avoided.

What is claimed is:

1. Low-coherence interferometric device for light optical depth scanning of an object positioned in front of a measurement aperture of the device by detecting the position of light reflecting sites which are located at different measurement depths within the object along a scanning path running into the object in a scanning direction having a low-coherence interferometer which comprises a low-coherence light source, a beam splitter, a reference reflector and a detector, wherein;

the light paths between the elements of the interferometer form interferometer arms, namely a light source arm between the light source and the beam splitter, an object arm between the beam splitter and the light-reflecting site in the object, a reference arm between the beam splitter and the reference reflector and a detector arm between the beam splitter and the detector;

measurement light is irradiated in the scanning direction, as primary light, into the object via the light source arm and the object arm and light reflected at the light-reflecting site in the object is directed, as secondary light, via the object arm and the detector arm to the detector;

reference light is directed from the beam splitter to the reference reflector and from there via the reference arm and the detector arm to the detector; and the measurement light and the reference light are combined in order to generate an interference signal when an optical path length of the measurement light path consisting of the light source arm, the object arm and the detector arm corresponds to the optical length of the reference light path consisting of the light source arm, the reference arm and the detector arm, wherein:

the interferometer is a free-space in-line interferometer comprising a beam splitter with a reflecting surface, said reflecting surface being oriented transverse to the scanning direction, the beam splitter splitting incident light into a component passing through said reflecting surface and a component reflected from said reflecting surface, the light source, the detector and the reference mirror being arranged on a side of the reflecting surface of the beam splitter facing away from the measurement aperture, the light source arm and the reference arm run at least in sections of the light source arm and of the reference arm adjacent to the beam splitter reflecting surface at the same angle to the beam splitter reflecting surface, a movable scanning lens is arranged between the beam splitter reflecting surface and the measurement aperture; and the movable scanning lens and the beam splitter are movable for depth scanning in the same direction and in synchronization.

2. Device according to claim 1, wherein the movable scanning lens and the beam splitter are fixed to each other and jointly movable.

3. Device according to any one of the preceding claims, wherein a detection lens (4) is arranged on the side of the beam splitter (8) facing away from the measurement aperture (12).

4. Device according to claim 1 comprising a stationary lens in a position adjacent to the scanning lens.

5. Device according to claim 1 wherein the light source is adapted to emit a beam light along a line running perpendicular to the direction of the beam.

6. Device according to claim 5, wherein the light source is adapted to emit light in a plane extending perpendicular to the direction of the beam.

7. Device according to claim 1 wherein the detector has a plurality of light-sensitive elements arranged along a line.

8. Device according to claim 7 wherein the detector has a plurality of light-sensitive elements distributed as a two-dimensional array in a plane.

9. Device according to claim 7, wherein the light-sensitive elements are arranged jointly together with light transmitter elements in a combined light transmitter-detector module.

10. Device according to claim 7, wherein an electronic focus-correcting circuit is provided by means of which the signals of the light-sensitive elements of the detector are selectively delayed relative to one another.

11. Device according to claim 1, wherein the numerical aperture of the light path by which the primary light is irradiated into the object is smaller than the numerical aperture of the light path by which the secondary light, reflected from the object, is detected.

12. Device according to claim 1 wherein the light source arm and the detector arm run approximately coaxially at least in the section adjacent to the reflecting surface of the beam splitter.

13. Device according to claim 12 wherein the angle between the optical axes of the light source arm and the detector arm is at most 20° in the section adjacent to the reflecting surface of the beam splitter.

* * * * *